US008865965B2

(12) United States Patent
Sato et al.

(10) Patent No.: US 8,865,965 B2
(45) Date of Patent: Oct. 21, 2014

(54) ABSORBENT ARTICLE WITH HIGH AND LOW DENSITY PORTIONS AND SKIN CARE AGENT THEREON

(75) Inventors: Nobuya Sato, Tochigi (JP); Mina Tomita, Tochigi (JP)

(73) Assignee: Kao Corporation, Tokyo (JP)

(*) Notice: Subject to any disclaimer, the term of this patent is extended or adjusted under 35 U.S.C. 154(b) by 248 days.

(21) Appl. No.: 13/508,904

(22) PCT Filed: Nov. 15, 2010

(86) PCT No.: PCT/JP2010/070291
§ 371 (c)(1),
(2), (4) Date: May 9, 2012

(87) PCT Pub. No.: WO2011/065247
PCT Pub. Date: Jun. 3, 2011

(65) Prior Publication Data
US 2012/0226250 A1    Sep. 6, 2012

(30) Foreign Application Priority Data

Nov. 24, 2009   (JP) .................................. 2009-266878
Nov. 1, 2010    (JP) .................................. 2010-245695

(51) Int. Cl.
*A61F 13/511*       (2006.01)
(52) U.S. Cl.
CPC . *A61F 13/51104* (2013.01); *A61F 2013/51117* (2013.01); *A61F 13/51113* (2013.01)
USPC .......................................... 604/380; 604/367
(58) Field of Classification Search
CPC ................... A61F 13/51108; A61F 13/51113
USPC .................................................. 604/380–382
See application file for complete search history.

(56) References Cited

U.S. PATENT DOCUMENTS 6,610,173 B1 * 8/2003 Lindsay et al. ............... 162/109
6,626,961 B1 * 9/2003 Everhart et al. ............. 8/115.51
(Continued)

FOREIGN PATENT DOCUMENTS

CN       1623605 A      6/2005
CN       1694669 A     11/2005
(Continued)

OTHER PUBLICATIONS

International Preliminary Report on Patentability for International Patent Application No. PCT/JP2010/070291, mailed Jul. 19, 2012.
(Continued)

*Primary Examiner* — Lynne Anderson
*Assistant Examiner* — Kathryn E Ditmer
(74) *Attorney, Agent, or Firm* — Birch, Stewart, Kolasch & Birch, LLP

(57) ABSTRACT

An absorbent article includes a liquid permeable topsheet (10), a liquid impermeable or water repellent backsheet, and an absorbent member interposed between these sheets. The topsheet (10) is formed of a nonwoven sheet having high density portions (13A) and low density portions (14A). Each high density portion (13A) and each low density portion (14A) are different in density from each other. The high density portions (13A) and the low density portions (14A) are arranged in planar directions of the topsheet (10). The low density portions (14A) have a larger amount of a skin care agent (5) applied thereto than the high density portions (13A).

11 Claims, 9 Drawing Sheets

(56) References Cited

U.S. PATENT DOCUMENTS

| | | |
|---|---|---|
| 8,450,556 B2 * | 5/2013 | Miyamoto et al. ............ 604/380 |
| 2001/0025162 A1 | 9/2001 | Roe et al. |
| 2004/0102750 A1 | 5/2004 | Jameson |
| 2004/0140047 A1 | 7/2004 | Sato et al. |
| 2004/0158215 A1 | 8/2004 | Kasai et al. |
| 2004/0242097 A1 | 12/2004 | Hasenoehrl et al. |
| 2006/0135920 A1 | 6/2006 | Virgilio et al. |
| 2008/0249491 A1 | 10/2008 | Young et al. |

FOREIGN PATENT DOCUMENTS

| | | |
|---|---|---|
| CN | 1722998 A | 1/2006 |
| CN | 101080209 A | 11/2007 |
| JP | 2004-174234 A | 6/2004 |
| JP | 2004-255166 A | 9/2004 |
| JP | 2008-86504 A | 4/2008 |
| JP | 2009-5860 A | 1/2009 |
| JP | 4286255 B2 | 6/2009 |
| WO | WO 99/12530 A1 | 3/1999 |
| WO | 00/61097 A1 | 10/2000 |
| WO | WO 2004/050000 A1 | 6/2004 |
| WO | WO 2004/058117 A1 | 7/2004 |
| WO | WO 2006/009995 A1 | 1/2006 |
| WO | WO 2006/066107 A1 | 6/2006 |
| WO | WO 2009028236 A1 * | 3/2009 |
| WO | WO 2012086476 A1 * | 6/2012 |

OTHER PUBLICATIONS

PCT/ISA/210—International Search Report dated Jan. 25, 2011, issued in PCT/JP2010/070291.

* cited by examiner

ABSORBENT ARTICLE WITH HIGH AND LOW DENSITY PORTIONS AND SKIN CARE AGENT THEREON

TECHNICAL FIELD

The present invention relates to absorbent articles, such as disposable diapers, sanitary napkins, panty liners (vaginal discharge sheet), and incontinence pads.

BACKGROUND ART

Wearing an absorbent article, such as a disposable diaper, a sanitary napkin, a panty liner (vaginal discharge sheet), or an incontinence pad, can cause a skin rash due to overhydration and the like. Absorbent articles containing a skin care product have been proposed to prevent a skin rash by the skin care effect of the skin care product.

For example, patent literature 1 below discloses an absorbent article having a lotion composition containing an emollient and an immobilizing agent applied to the topsheet thereof in a non-uniform pattern. Patent literature 2 below describes a disposable absorbent article having a lotion applied to the liquid pervious topsheet thereof in the form of a pattern of a plurality of stripes that are separated by a plurality of areas having no lotion. The pattern of a plurality of stripes is a discontinuous pattern.

Patent literature 3 below assigned to the assignee of the present application proposes applying a diamide derivative having a specific structure to a region of an absorbent article that comes into contact with the skin of a wearer while the absorbent article is worn. The diamide derivative is transferable to the skin of a wearer to function as an oily skin care agent.

CITATION LIST

Patent Literature

Patent literature 1: U.S. 2008/249491A1
Patent literature 2: U.S. 2006/135920A1
Patent literature 3: US 2004/158215A1

SUMMARY OF INVENTION

Technical Problem

Patent literatures 1 and 2 teach partial application of a lotion composition, which corresponds to a skin care agent, to a topsheet in a prescribed pattern.

However, application of a large quantity of a skin care agent to a topsheet in an attempt to produce an enhanced skin care effect often adversely affects the liquid permeability essentially possessed of the topsheet, leaving room for improvement to obtain an enhanced skin care effect.

Solution To Problem

The invention provides an absorbent article including a liquid permeable topsheet, a liquid impermeable or water repellent backsheet, and an absorbent member arranged between the topsheet and the backsheet. The topsheet is formed of a nonwoven sheet having high density portions and low density portions. Each high density portion and each low density portion are different in density from each other. The high density portions and the low density portions are arranged in planar directions of the topsheet. The low density portions have a larger amount of a skin care agent applied thereto than the high density portions.

Advantageous Effects of Invention

The absorbent article of the invention is capable of containing a large amount of a skin care agent while retaining good liquid permeability of the topsheet.

DESCRIPTION OF EMBODIMENTS

The invention will be described based on its preferred embodiments with respect to the accompanying drawings.

Figure 1:
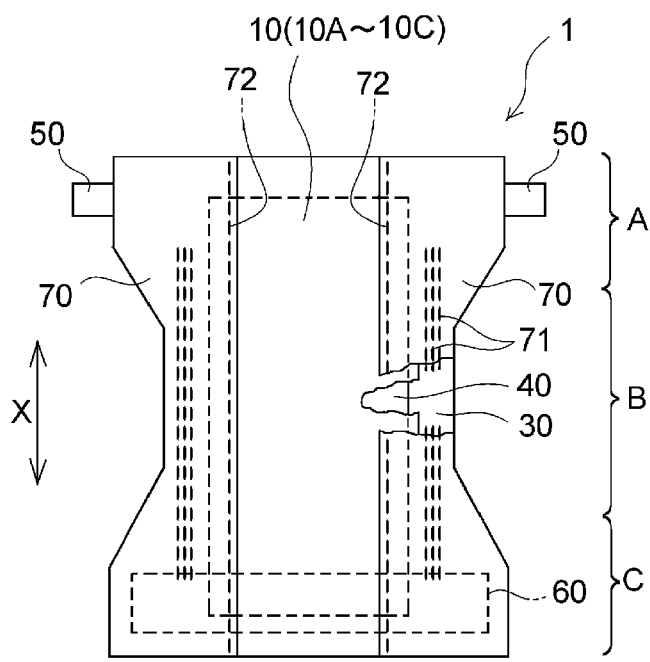
FIG. 1 is a plane of a disposable diaper illustrating a basic structure common to first to fourth embodiments of the invention, with part cut away.

FIG. 1 is a plan of a disposable diaper according to a first embodiment of the invention, with a part cut away. As shown in FIG. 1, the disposable diaper of the first embodiment (hereinafter simply referred to as a diaper 1) includes a liquid permeable topsheet 10, a liquid impermeable or water repellent backsheet 30, and an absorbent member 40 interposed between the two sheets.

The diaper 1 has along its longitudinal direction a rear section A adapted to be worn about the back of a wearer, a crotch section B adapted to be worn about the crotch of a wearer, and a front section C adapted to be worn about the front of a wearer while worn.

The diaper 1 also has a side sheet 70 formed of water repellent nonwoven fabric disposed on each lateral side thereof to cover each lateral side portion of the topsheet 10. The topsheet 10 and each side sheet 70 are bonded to the backsheet 30 along their portions outward from the perimeter of the absorbent member 40. A leg flap outward from each side edge of the absorbent member 40 has elastic members 71 to form a leg gather. Each side sheet 70 has an elastic member 72 disposed along its proximal side edge in the diaper lateral direction to form a standing gather.

The diaper 1 is of what we call an open-style type or a taped type, which is put on a wearer by fastening a pair of fastening tapes 50, 50 onto a landing tape 60 provided on the outer side of the front section C. The backsheet 30, absorbent member 40, fastening tapes 50, landing tape 60, side sheets 70, and elastic members 71, 72 may be of any materials commonly employed in this type of articles. For example, the absorbent member 40 may be an aggregate of a fibrous material, such as pulp fiber. The aggregate may contain particles of an absorbent polymer and the like or may be wrapped in tissue or water pervious nonwoven fabric.

Figure 2:
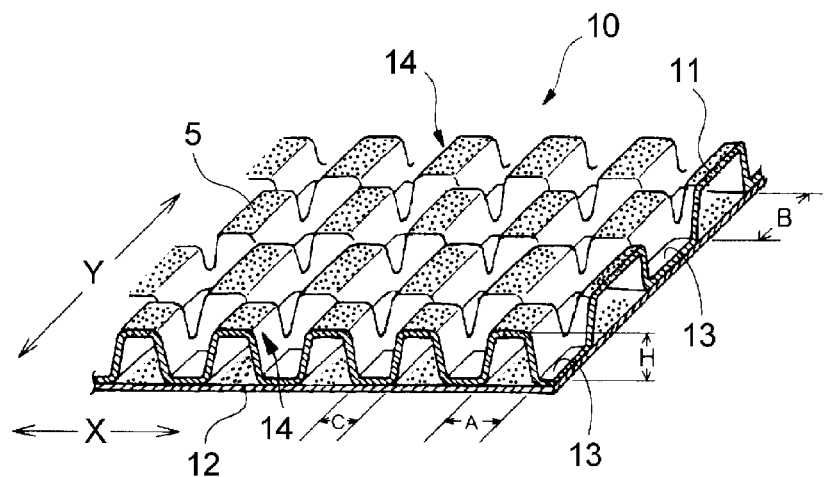
FIG. 2 is a perspective of a topsheet used in the first embodiment.

As shown in FIG. 2, the topsheet 10 used in the first embodiment is formed of a nonwoven sheet material composed of an upper nonwoven fabric 11 facing the skin of a wearer and a lower nonwoven fabric 12 facing the absorbent member 40. The upper nonwoven fabric 11 and the lower nonwoven fabric 12 are partially bonded to each other at a large number of bonds 13. The upper nonwoven fabric 11 bulges toward the wearer's skin at portions other than the bonds 13 to form a large number of hollow protrusions 14. As shown in FIG. 2, between adjacent protrusions 14, 14 there is a depression, and every bond 13 is formed in the bottom of the depression. The protrusions 14 and the bonds 13 alternate with each other in one direction to make a plurality of lines. The upper nonwoven fabric 11 is formed of a substantially inextensible sheet material. The lower nonwoven fabric 12 is formed of a substantially inextensible sheet material. Each protrusion 14 depicted in FIG. 2 has a rectangular base. The shape of each protrusion 14 is generally a flattened rectangular parallelepiped or a truncated four-sided pyramid with rounded lateral edges in either case. Each bond 13 is rectangular. Examples of the nonwoven sheet material that can be used in the invention include a single-ply nonwoven fabric, a multi-ply nonwoven fabric composed of two or more layers, and a sheet material formed by partially bonding two nonwoven fabrics in a prescribed pattern while forming spaces in parts between the two nonwovens as used in the present embodiment.

The protrusions 14 and the bonds 13 alternate in a direction to make a plurality of lines. In the present embodiment, the protrusions 14 and the bonds 13 alternate in direction X indicated in FIG. 2. The direction X is coincident with the machine direction in the hereinafter described step of making a three-dimensional sheet material 10' and a topsheet 10. The direction X is also coincident with the longitudinal direction of the diaper 1 (absorbent article) in which the topsheet 10 is assembled. The plurality of lines each composed of the alternating protrusions 14 and bonds 13 are arranged parallel in direction Y indicated in FIG. 2.

Upon focusing on any one of the protrusions, called protrusion A, of any one of the lines (extending in direction X), called line A, each line adjacent to the line A has no protrusion located at the same position in direction X as the protrusion A. To have no protrusion at the same position means that the adjacent lines have no protrusion located at completely the same position as the protrusion A. That is, any protrusions of every pair of adjacent lines are not arranged to completely continue in the diaper lateral direction (direction Y). Accordingly, either both a part of a protrusion and a part of a bond or only a bond of a line adjacent to the line A may be located at the same position in direction X as the protrusion A of the line A. If protrusions should be arranged to completely continue to each other in direction Y of the diaper 1, there will be formed a long protrusion (ridge) extending in direction Y, along which a bodily fluid can flow to cause a leak. In the example shown, bonds of two adjacent lines are offset with respect to each other by half a pitch. Accordingly, upon focusing on one protrusion 14 (protrusion A) of one line, the protrusion A is surrounded by bonds 13 in four directions. In brief, the bonds 13 and the protrusions 14 are arranged in a staggered pattern.

The topsheet 10 has, in its planar directions, bonded regions 13A where the two nonwoven fabrics 11 and 12 are bonded to form the bonds 13 and protruded regions 14A where the two nonwoven fabrics 11 and 12 are not bonded together with the upper nonwoven fabric 11 forming protrusions 14. The individual protruded regions 14A have a lower density than the individual bonded regions 13A.

The term "planar direction" as used for the topsheet 10 and the hereinafter described three-dimensional sheet material 10' indicates a direction parallel to the upper and lower surfaces of the sheets.

In the cases when the protrusions 14 are hollow as in the present embodiment, the density of the individual protruded regions 14A of the topsheet 10 or the three-dimensional sheet material 10' is a value calculated without reckoning the volume of the hollow space.

Figure 3:
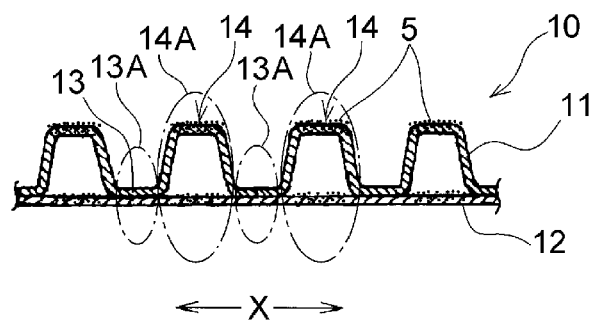
FIG. 3 is a cross-section along direction X of the topsheet used in the first embodiment.

In the topsheet 10 of the present embodiment, each bonded region 13A and each protruded region 14A correspond to each high density portion and each low density portion, respectively, which are different in density. As shown in FIG. 3, the topsheet 10 has a skin care agent 5 applied on the protruded regions 14A, which are low density portions, in a larger amount than on the bonded regions 13A, which are high density portions. As used herein, the term "apply" is intended to include the operation of coating the surface of a nonwoven fabric with a skin care agent and the operation of impregnating or otherwise incorporating a skin care agent into the inside of nonwoven fabric or a nonwoven sheet. In the present embodiment, a skin care agent 5 is present in both the upper nonwoven fabric 11 and the lower nonwoven fabric 12 in the protruded regions 14A by the hereinafter described method. When a skin care agent is said to be applied (or present) "in a larger amount", the "amount" is meant to be an amount per same size area of a topsheet (e.g., 0.5 to 10 $g/m^2$). The expressions "applied (or present) to a low density portion in a larger amount than to a high density portion" is intended to mean that the high density portion contains no skin care agent or a smaller amount of the skin care agent than the low density portion does.

The diaper 1 of the present embodiment is used in the same manner as with ordinary open-type diapers. The topsheet 10 is assembled into the diaper 1 with its upper nonwoven fabric 11 facing the wearer's skin and the lower nonwoven fabric 12 facing the absorbent member 40.

In the topsheet 10 of the diaper 1 of the present embodiment, the protruded region 14A, which is a low density portion, has larger interfiber spaces than the bonded region 13A, which is a high density portion. Since the low density portions have larger interfiber spaces than the high density portions, the topsheet 10A is able to retain a larger amount of the skin care agent in the low density portions thereof than in the high density portions. If the high density portions with smaller interfiber spaces are configured to contain a large amount of the skin care agent, the presence of a large amount of the skin care agent in the high density portions is liable to adversely affect the liquid permeability. Such a problem is less likely to occur when the skin care agent is held in the low density portions as in the present embodiment.

The topsheet 10 of the diaper 1 of the present embodiment has the bonded regions 13A, which are high density portions, and the protruded regions 14A, which are low density portions, arrayed in planar directions thereof. As stated, one protrusion 14 is surrounded by depressions in four directions. In other words, one protruded region 14A, which is a low density portion, is surrounded by the bonded regions 13A, which are high density portions. More specifically, every bonded region 13A, which is a high density portion, is located between two protruded regions 14A, which are low density portions, in a first planar direction (direction X) of the topsheet 10 and between two protruded regions 14A, which are low density portions, in a second planar direction (direction Y) perpendicular to the first direction.

With a skin care agent held in the low density portions, which have a low density and are soft, the low density portions provide a soft fit to the skin and achieve promoted transfer of the skin care agent to the skin. Since every low density portion is surrounded by the high density portions, the skin care agent is prevented from moving on the topsheet. Besides, this geometry is suited to apply a requisite amount of the skin care agent to the skin.

In arranging the high and the low density portions in planar directions of the topsheet 10, it is preferred that the area of the low density portions be larger than that of the high density portions in a plan view to ensure transfer of the skin care agent to the skin so that a sufficient amount of the skin care agent may be transferred to the skin even with a reduced amount of the skin care agent applied per unit area. The area ratio of the low density portions to the high density portions is preferably about 2 to 20, more preferably about 4 to 10.

As shown in FIGS. 2 and 3, the topsheet 10 of the present embodiment has the protruded regions 14A (low density portions) spacedly arrayed in a first planar direction (direction X) to make a plurality of lines of the low density portions. The lines are arrayed in a second planar direction perpendicular to the first direction (direction Y). There must be a protruded region 14A (low density portion) located somewhere in the second direction (direction Y) when seen from any position in the first direction (direction X).

That is, there is no area without a protruded region 14A (low density portion) over the total length in the second direction (direction Y). By this geometry, the topsheet is ready to have the protruded regions 14A (low density portions) deformed in conformity to wearer's anatomy thereby to achieve good transfer of the skin care agent to the wearer's skin.

While the protruded regions 14A (low density portions) form skin contact regions that are brought into contact with the skin, the bonded regions 13A (high density portions) provide non-skin-contact regions that are not brought into contact with the skin.

Thus, while the high density portions secure the sheet strength and form non-skin-contact regions, the low-density soft regions with a large amount of a skin care agent applied thereto form skin contact regions that are gently applied to the skin to cause the skin care agent to be transferred to the skin.

As stated, the topsheet 10 of the present embodiment has a skin care agent 5 applied to both the upper and the lower nonwoven fabric 11, 12 located in the protruded regions 14A by the hereinafter described method. Making a comparison between the upper nonwoven fabric 11 and the lower nonwoven fabric 12 in the protruded regions 14A, the amount per same size area of the skin care agent 5 attached to the former is larger than that attached to the latter as shown in FIG. 3.

Making a comparison between the lower nonwoven fabric 12 in the protruded regions 14A and the bonded regions 13A, the amount per same size area of the skin care agent 5 attached to the former is larger than that attached to the latter as shown in FIG. 3.

The topsheet having a larger amount of a skin care agent 5 in its upper nonwoven fabric 11 that defines the skin contact side of the protruded regions 14 than in its lower nonwoven fabric 12 achieves good transfer of the skin care agent 5 to the skin and therefore exhibits a high skin care effect.

The presence of the skin care agent on/in the lower nonwoven fabric 12 in the protruded regions 14, even in a small amount, helps the skin care agent 5 to continue being held on the skin contact side to achieve prolonged duration of the skin care effect.

Furthermore, the presence of the skin care agent on/in the lower nonwoven fabric 12 in the protruded regions 14 helps the skin care agent to continue being held even when the protrusions are collapsed under the load of the wearer.

It is preferred that the density of the lower nonwoven fabric 12 in the protruded regions 14A be equal to or greater than that of the upper nonwoven fabric 11 in the protruded regions 14A.

Any skin care agent that has a protective, a healing or a like effect on the wearer's skin can be used in the invention. Preferred skin care agents are exemplified by diamine derivatives represented by formula (I) below and described in patent literature 3 listed supra.

[Chem. 1]

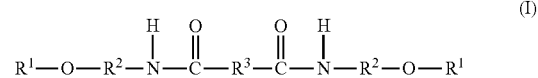

(I)

wherein $R^1$ is a straight-chain or branched C1-C22 hydrocarbon group optionally substituted with hydroxyl and/or alkoxy; $R^2$ is a straight-chain or branched C1-C12 divalent hydrocarbon group; and $R^3$ is a straight-chain or branched C1-C42 divalent hydrocarbon group, a straight-chain or branched C11-C42 alkylene group, or an alkenylene group having 1 to 4 double bonds.

The diamide derivative of formula (I) is a compound described in WO 00/61097 and has a medicinal benefit that improves the water retention ability and barrier function of a keratin layer. The diamide derivative retained in the high density portions transfers to the skin of a wearer wearing the absorbent article to function as an oily skin care agent that minimizes and/or improves a ski rash.

The diamide derivatives may be used either individually or in combination of two or more thereof.

Oily skin care agents that can be used in the invention further include those known as an emollient in the field of cosmetics.

Examples of such oily skin care agents include liquid paraffin, silicone oil, animal and vegetable oils (e.g., olive oil, jojoba oil, safflower oil, squalane, and squalene), monoglycerides, diglycerides, triglycerides, aliphatic ethers (e.g., myristyl 1,3-diemthylbutyl ether, palmityl 1,3-dimethylbutyl ether, stearyl 1,3-dimethylbutyl ether, palmityl 1,3-methylpropyl ether, and stearyl 1,3-methylpropyl ether), isostearyl cholesterol ester, paraffin wax, C12-C22 fatty acids, C12-C44 fatty acid ethers, C12-C22 fatty alcohols, vaseline, fatty acid sorbitan esters which are the monoesters, diesters, or triesters, polyoxyethylene fatty acid sorbitan esters which are the monoesters, diester, or triesters, metal soaps (e.g., magnesium stearate), sucrose fatty acid esters, cyclodextrin fatty acid esters, silicones, silicone resins, and the emollient agents or the lotions containing an emollient agent and a fixing agent described in patent literatures 1 and 2.

These skin care agents may be used either individually or as a combination of two or more thereof.

The topsheet 10 used in the present embodiment is obtained by forming a three-dimensional sheet material 10' by, for example, the method taught in JP 2004-174234A for producing a topsheet of an absorbent article and applying a skin care agent to the three-dimensional sheet material 10' such that the skin care agent is attached preferentially to the protruded regions 14A.

Figure 4:
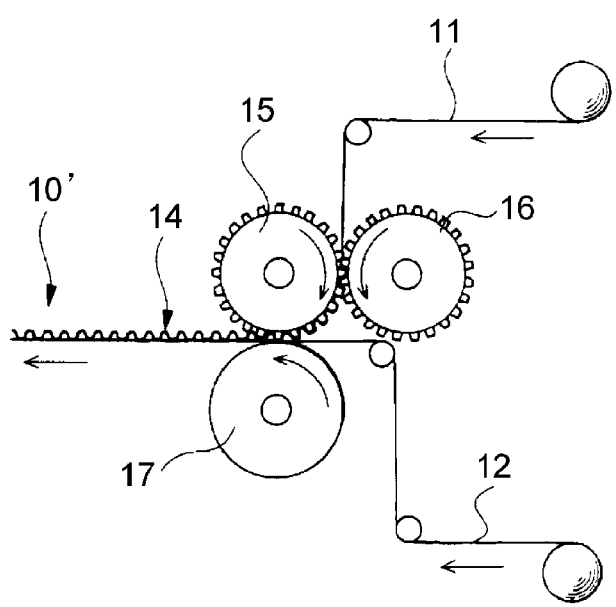
FIG. 4 is a schematic view illustrating the step of forming a three-dimensional sheet material used in a preferred method for making the topsheet of the first embodiment.

In a preferred example of the production of the topsheet 10, an upper nonwoven fabric 11 that is substantially inextensible is three-dimensionally textured by its passage through the nip between a first roller 15 having an engraved peripheral surface and a second roller having an engraved peripheral surface intermeshing with that of the first roller 15 as shown in FIG. 4. The thus textured nonwoven fabric 11 is held to the periphery of the first roller 15 by suction and, in the meantime, a lower unwoven fabric 12 that is substantially inextensible is superposed on the nonwoven fabric 11 and bonded to the parts of the upper nonwoven fabric 11 that are located on the projections of the engraved first roller 15 to provide a three-dimensional sheet material 10' having protrusions 14.

In the method shown in FIG. 4, the three-dimensional sheet material 10' is obtained by partially applying heat and pressure to the upper nonwoven fabric 11 and the lower nonwoven fabric 12 between the protrusions on the first roller 15 and the smooth surface of a heat roller 17. Therefore, the resulting three dimensional sheet material 10' has high density regions having bonds 13 (bonded regions 13A) and relatively low density regions other than the bonds (protruded regions 14A) arranged in its planar directions.

Figure 5A:
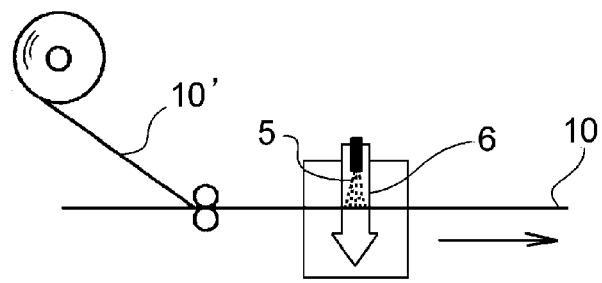
FIG. 5 is a schematic view illustrating the step of applying a skin care agent in the preferred method for making the topsheet of the first embodiment.
Figure 5B:
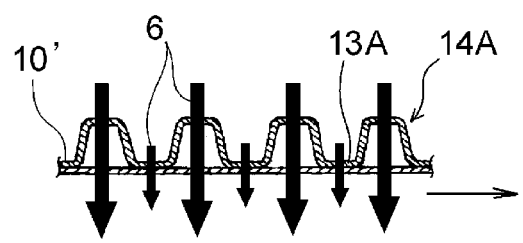

Subsequently, a skin care agent 5 is applied preferentially to the protruded regions 14A of the three dimensional sheet material 10'. Specifically, as shown in FIG. 5(a), a skin care agent 5 is sprayed to the three dimensional sheet material 10' from one side while sucking air 6 containing the atomized skin care agent 5 from the other side of the three dimensional sheet material 10'. Because the three dimensional sheet material 10' has a higher air permeability in the low-density protruded regions 14A than in the high-density bonded regions 13A, air 6 containing the skin care agent 5 passes in a larger quantity through the protruded regions 14A than through the bonded regions 13A as shown in FIG. 5(b). As a result, the skin care agent 5 is attached to the protruded regions 14A more than to the bonded regions 13A.

In that way, there is provided a topsheet 10 having the skin care agent 5 attached to the protruded regions 14A (low density portions) in a larger amount than to the bonded regions 13A (high density portions). For the details of the method for producing the three dimensional sheet material 10', reference may be made to JP2004-174234A.

The sheet materials forming the upper nonwoven fabric 11 and the lower nonwoven fabric 12 may be any of sheet materials conventionally used to make the topsheet of absorbent articles, such as disposable diapers and sanitary napkins. Useful nonwoven fabrics include a nonwoven fabric prepared by consolidating a carded web of staple fibers by through-air bonding, heat roll bonding, resin bonding, hydroentangling, needle punching, or a like technique; a nonwoven fabric prepared by consolidating continuous fibers by heat roll bonding, hydroentanglement, or a like technique (e.g., spun-bonded nonwoven); a nonwoven fabric obtained by directly converting stable fibers into nonwoven web form (e.g., melt-blown nonwoven); and a nonwoven fabric obtained by converting an airlaid web of stable fibers into nonwoven web form by through-air bonding, resin bonding, or a like technique. The means for bonding fibers to make the nonwoven fabrics is not particularly limited and include, for example, bonding using a binder and thermal bonding. The fibers may be consolidated by mechanical entanglement, such as hydroentanglement, instead of the bonding described. The nonwoven fabrics are preferably made of fibers having a fineness of 1 to 20 dtex, more preferably 1.5 to 4 dtex, to secure the topsheet strength and to improve the feel to the touch. It is preferred to use substantially inextensible nonwoven fabrics as the upper and the lower nonwoven fabrics 11 and 12, particularly as the upper nonwoven fabric 11.

Examples of the fibers used to make the upper and the lower nonwoven fabrics 11 and 12 include, but are not limited to, synthetic fibers, such as polyolefins, e.g., polyethylene (PE) and polypropylene (PP), polyesters, e.g., polyethylene terephthalate (PET), and polyamides, e.g., nylon; regenerated cellulose fibers, such as rayon and cuprammonium; and natural fibers, such as cotton. Conjugate fibers, such as sheath-core conjugate fibers (having low-melting fiber as a sheath and high-melting fiber as a core), side-by-side conjugate fibers, and splittable conjugate fibers, are also used preferably. These fibers may be used either individually or as a combination of two or more thereof. The upper nonwoven fabric 11 and the lower nonwoven fabric 12 may be the same or different. The fibers making the upper nonwoven fabric 11 and those making the lower nonwoven fabric 12 may be the same or different.

The protrusions 14 of the topsheet 10 preferably have a height H (see FIGS. 2) of 0.5 to 5 mm, more preferably 1 to 4 mm. The bottom (or base) of each protrusion 14 preferably has a length A in direction X (the direction of each line) of 2 to 30 mm, more preferably 2 to 5 mm, a length B in direction Y (perpendicular to the direction of each line) of 2 to 30 mm, more preferably 2 to 5 mm, and an area of 4 to 900 mm$^2$, more preferably 4 to 25 mm$^2$. Each bonded portion 13 preferably has a bond length C (see FIG. 2) in direction X (the direction of each line) of 0.1 to 20 mm, more preferably 0.5 to 5 mm. The plan-view shape of the individual protruded portions 14 is not limited to a rectangle and may be, for example, a circle, an elongated circle, a rhombus, or a triangle.

While, in the first embodiment described above, the topsheet 10 is used with the direction of lines of alternating protruded portions 14 and the bonded portions 13 (direction X) substantially coincident with the longitudinal direction of the diaper 1, it may be disposed with the direction of lines of alternating protruded portions 14 and the bonded portions 13 (direction X) substantially coincident with the lateral direction of the diaper 1.

The invention will then be described with reference to a second to a fourth embodiment. The absorbent articles of the second to the fourth embodiment have the same structure as in the first embodiment except for the topsheet. The description of the first embodiment applies to the undescribed details of the second to fourth embodiments.

Figure 6:
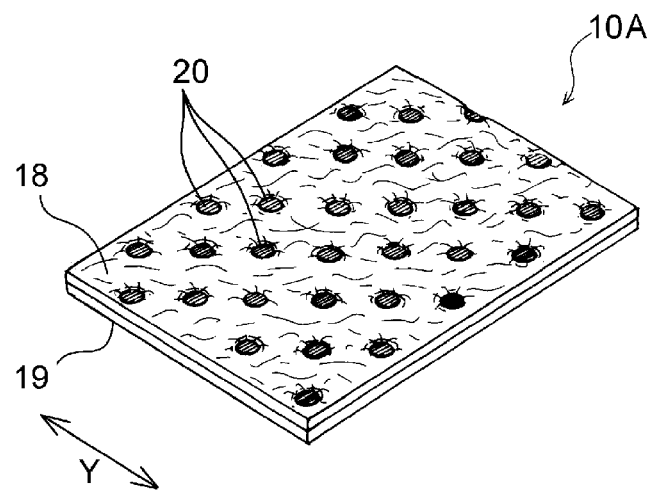
FIG. 6 is a perspective of a topsheet used in the second embodiment.
Figure 7:
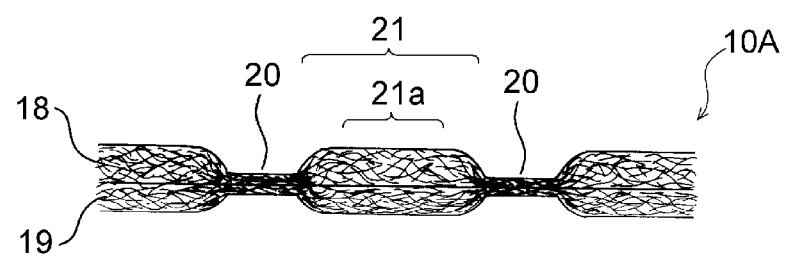
FIG. 7 is a cross-section along direction Y of the topsheet used in the second embodiment.

As shown in FIG. 6, a topsheet 10A according to the second embodiment is formed of a stack of nonwoven fabrics including an upper fiber layer 18 and a lower fiber layer 19. The two fiber layers 18 and 19 are bonded together at debossed portions 20 arranged in a staggered pattern. Each debossed portion 20, formed by compressing the upper fiber layer 18 and the lower fiber layer 19 into a unitary sheet, is a high density portion having a higher density than the rest of the topsheet, i.e., non-debossed regions 21, particularly than the central portion 21a of each non-debossed region 21 surrounded by four debossed regions 20. That is, the debossed portions 20 which are formed by compression are high density portions, while the non-debossed regions 21, particularly the central portion 21a of the individual non-debossed regions 21, are low density portions. The high density portions and the low density portions are arranged in the planar directions of the topsheet 10A.

The topsheet 10A of the second embodiment is assembled into a diaper with its upper fiber layer 18 facing the wearer's skin and the lower fiber layer 19 facing the absorbent member 40.

In the second embodiment, too, a larger amount of a skin care agent is present in the non-debossed regions 21 (particularly the central portions 21a), which are low density portions, than in the debossed regions 20, which are high density portions. Since the non-debossed regions 21 (low density portions), particularly the central portions 21a have larger interfiber spaces than the debossed regions 20 (high density portions), the topsheet 10A is able to contain a larger amount of the skin care agent in the low density portions than in the high density portions. If the high density portions with smaller interfiber spaces are configured to contain a large amount of the skin care agent, it is likely that the skin care agent fills the interfiber spaces to adversely affect the liquid permeability. Such a problem is less likely to occur when the skin care agent is held in the low density portions.

The topsheet 10A of the second embodiment is produced by, for example, superposing the upper and the lower fiber layer 18 and 19 on each other, embossing the stack of the two layers to form debossed portions 20 by passing the stack through an embossing unit including an embossing roller having projections on its peripheral surface and a counter anvil roller having a smooth surface, and applying a skin care agent preferentially to the non-debossed regions 21 of the stack by the same preferred method for making the topsheet 10 of the first embodiment. The embossing processing may be embossing with no heat application, heat embossing, ultrasonic embossing, high frequency embossing, or the like. Embossing processing is preferably performed at or below the melting point of the fibers constituting the topsheet 10A.

The upper and the lower fiber layer 18 and 19 used in the second embodiment may be any of the nonwovens hereinabove described for use as the upper and the lower nonwoven fabric 11 and 12 of the first embodiment. A stack of two carded webs or a stack of a non-consolidated carded web and a nonwoven fabric may be used to be subjected to embossing followed by skin care agent application as described.

Figure 8:
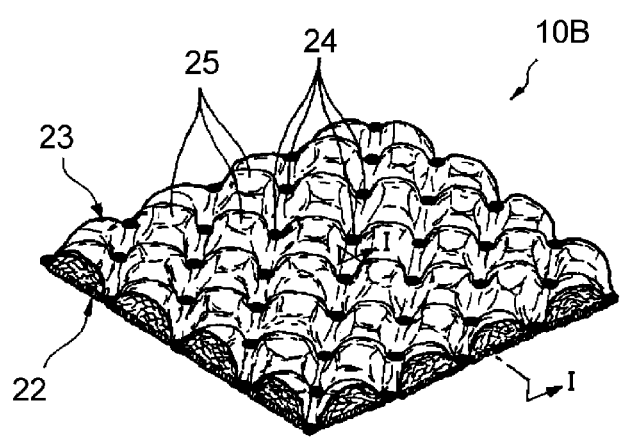
FIG. 8 is a perspective of a topsheet used in the third embodiment.
Figure 9:
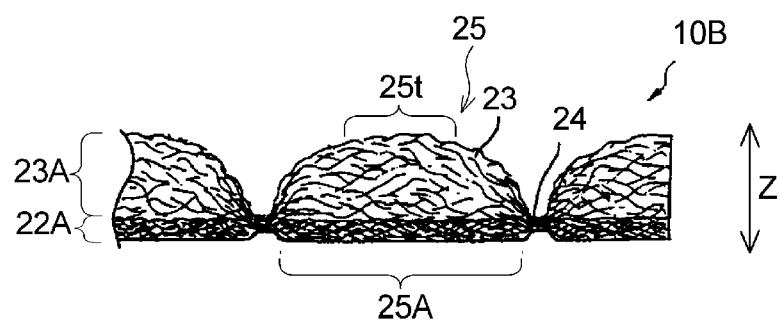
FIG. 9 is an enlarged cross-section along line I-I of the topsheet shown in FIG. 8.

As shown in FIGS. 8 and 9, a topsheet 10B of the third embodiment is formed of a stack of nonwoven fabrics composed of a lower fiber layer 22 containing heat-shrunken fibers (heat-shrinkable fibers having thermally shrunken) and an upper fiber layer 23 made of non-heat-shrinkable fibers. The two fiber layers 22 and 23 are integrated in their thickness direction into a unitary sheet by a large number of fusion bonds discretely formed by heat fusion. The lower fiber layer 22 has thermally shrunken due to the shrinkage of the heat-shrinkable fibers between adjacent fusion bonds 24 to cause the upper fiber layer 23 to bulge toward the skin of a wearer. As a result, the upper fiber 23 has a large number of protrusions 25.

Any known heat-shrinkable fibers may be used to cause the lower fiber layer 22 to shrink. Self-crimping fibers are preferred. Self-crimping fibers have potential crimp and are capable of shrinking through development of helical crimp on heat application. Self-crimping fibers are formed of, for example, conjugate fibers composed of two thermoplastic polymers having different shrinkage percentages in a sheath-core or side-by-side configuration, such as those described in JP9-296325A and Japanese Patent 2759331. A preferred example of the two thermoplastic polymers having different shrinkage percentages is a combination of an ethylene-propylene random copolymer (EP) and polypropylene (PP). The lower fiber layer 22 may be made solely of the heat-shrinkable fibers or may contain other fibers. In the latter case, the proportion of the heat-shrinkable fibers in the lower fiber layer 22 is preferably at least 50%, more preferably 70% to 90%, by mass.

The term "non-heat-shrinkable fibers" as used for the fibers contained in the upper fiber layer 23 is intended to include fibers having no heat shrinkability and fibers having heat shrinkability but substantially incapable of shrinking at or below the shrink onset temperature of the heat-shrinkable fibers contained in the lower fiber layer. The upper fiber layer 23 preferably contains heat fusible fibers containing a heat fusible resin having a melting temperature Tm higher than the heat shrink onset temperature Ts of the het-shrinkable fibers contained in the lower fiber layer 22. The proportion of the heat fusible fibers in terms of the heat fusible resin in the upper fiber layer 23 is preferably at least 70%, more preferably 80% or more, by mass. It is most preferred that 100% of the non-heat-shrinkable fibers making up the upper fiber layer 23 be the heat fusible fibers.

The top sheet 10B has the lower fiber layer 22 thermally shrunken to gain density. On the other hand, the upper fiber layer 23 forms protrusions with the shrinkage of the lower fiber layer 22 and, as a result, the density of the upper fiber layer 23 tends to decrease. As shown in FIG. 9, the density of a protruded region 25A defined to be a region having one protrusion 25 in planar directions is the highest in the lower fiber layer 22 and gradually decreases in the upper fiber layer 23 toward the top of the protrusion 25 to reach the lowest in the top portion 25t of the protrusion 25.

The topsheet 10B of the third embodiment is assembled into a diaper with its upper fiber layer 23 facing the wearer's skin and the lower fiber layer 22 facing the absorbent member 40.

In the topsheet 10B of the third embodiment, the top portion 25t of the individual protrusions 25 corresponds to the low density portion, and the fusion bond 24 present in the bottom of the individual depressions located between adjacent protrusions 25 corresponds to the high density portion. The high density portions and the low density portions are arranged in the planar directions of the topsheet 10B. There is a region between the top portion 25t and the fusion bond 24 in a planar direction of the topsheet 10B, the density of which region is intermediate between the densities of the top portion 25t and the fusion bond 24, and which region surrounds the top portion 25t of the protrusion.

The topsheet 10B of the third embodiment contains a larger amount of a skin care agent in the top portion 25t of every protrusion 25, which is the low density portion, than in the fusion bond 24, which is the high density portion. Since the top portions 25t (low density portions) have larger interfiber spaces than the fusion bonds 24 (high density portions), the topsheet 10B is able to contain a larger amount of a skin care agent in the low density portions than in the high density portions. If the high density portions with smaller interfiber spaces are configured to contain a large amount of the skin care agent, it is likely that the skin care agent adversely affects the liquid permeability. Such a problem is less likely to occur when the skin care agent is held in the low density portions as in the present embodiment.

The topsheet 10B of the third embodiment contains a larger amount of the skin care agent in its portion 23A, which is a low density portion formed of the upper fiber layer 23, particularly the top portion 25t of the protrusion than in its portion 22A, which is a high density portion formed of the lower fiber layer 22. Since the portion 23A (low density portion) of the upper fiber layer 23 has larger interfiber spaces than the portion 22A (high density portions) of the lower fiber layer 22, the topsheet 10B is able to contain a larger amount of a skin care agent in the low density portions than in the high density portions. If the high density portions with smaller interfiber spaces are configured to contain a large amount of the skin care agent, it is likely that the skin care agent adversely affects the liquid permeability. Such a problem is less likely to occur when the skin care agent is held in the low density portions as in the present embodiment.

Since the topsheet 10B of the third embodiment contains a larger amount of a skin care agent in the low density portions than in the high density portions, both the low and the high density portions being distributed in the planar directions and/or the thickness direction (direction Z), and is used with its bulky and soft low density portions in contact with the skin of a wearer, it is deformable in conformity to the wearer's body and able to have an as-needed skin care agent contained in its low density portions transferred to the entire skin in contact.

The nonwoven sheet forming the topsheet 10B has a multi-layered structure in its low density portions arranged in its planar directions and contains a larger amount of a skin care agent in the upper layer (the upper fiber layer 23) defining the skin contact side than in the lower layer (lower fiber layer 22) defining the side facing the absorbent member. Therefore, it is possible to configure the topsheet so as to stably hold the skin care agent in the low density portions by properly selecting the resin material of the fibers, the thickness of the fibers, or a mixing ratio of fibers different in material and/or thickness in making the topsheet. The above described structure is also advantageous in that the topsheet is ready to transfer the skin care agent as needed while worn without losing the skin care agent to the absorbent member.

In the topsheet 10B of the third embodiment, too, the low density portions form the skin contact regions that are brought into contact with the skin, while the high density portions form non-skin-contact regions that are not brought into contact with the skin.

Thus, while the high density portions secure the sheet strength and form non-skin-contact regions, the low-density soft regions with a large amount of a skin care agent applied thereto form skin contact regions that are gently applied to the skin to cause the skin care agent to be transferred to the skin. Since the lower layer provides a continuous high density region to secure the sheet strength of the topsheet 10B, the low density portions are permitted to have sufficient bulk and a low density and thereby to exhibit the effects expected of the low density portions.

As shown in FIGS. 10 through 13, a topsheet 10C of the fourth embodiment is formed of a stack of two nonwoven fabrics, i.e., an upper nonwoven fabric 11 forming the skin contact side of a diaper (the side facing the skin of a wearer) and a lower nonwoven fabric 12 forming the side facing the absorbent member 40.

Figure 10:
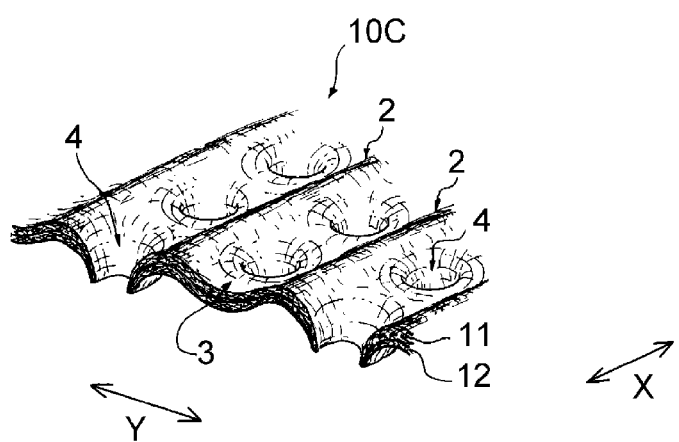
FIG. 10 is a perspective of a topsheet used in the fourth embodiment.
Figure 11:
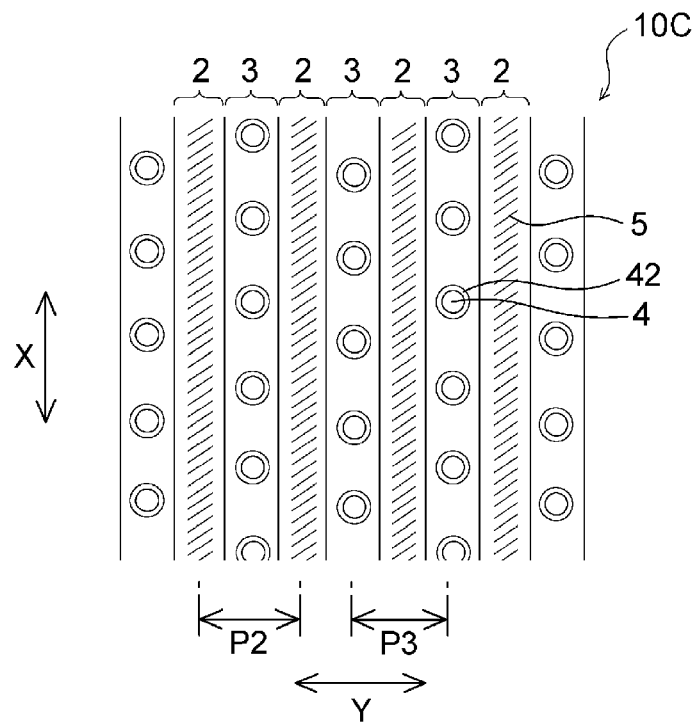
FIG. 11 is a plan of the topsheet used in the fourth embodiment.
Figure 12:
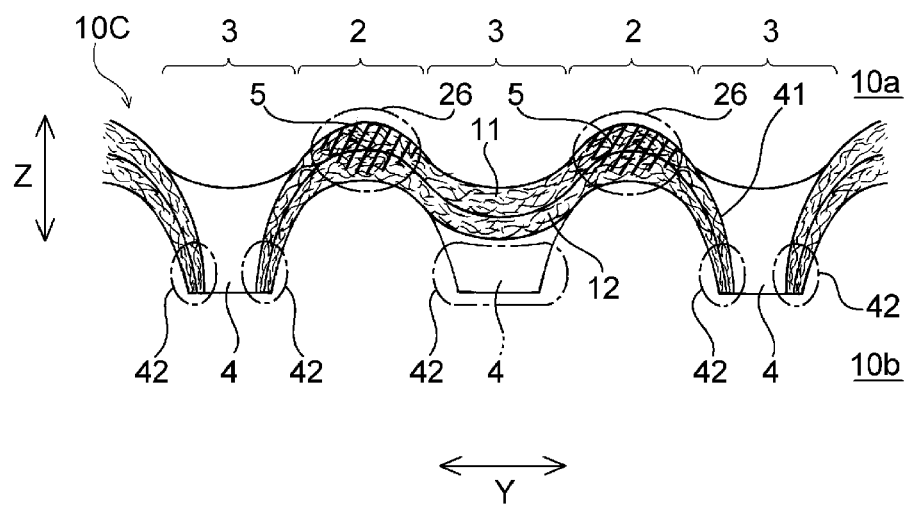
FIG. 12 is a cross-section along direction Y of the topsheet used in the fourth embodiment.

As shown in FIGS. 10 and 11, the topsheet 10C of the fourth embodiment has a large number of ridges 2 extending in the diaper longitudinal direction (direction X) on its skin contact side with valleys 3 between adjacent ridges 2, 2. The ridges 2 and the valleys 3 alternate in direction Y with no flat region in between. In a cross-sectional view taken along direction Y, each ridge 2 has an arcuate convex surface, and each valley 3 has an arcuate concave surface. The extending direction of the ridges 2 and the valleys 3 is the same as the machine direction (MD) in the production of the topsheet. Each of the pitch P2 of the ridges and the pitch P3 of the valleys 3 in the direction perpendicular to their extending direction is preferably 1.0 to 6.0 mm, more preferably 1.7 to 3.7 mm.

As shown in FIGS. 10 and 11, the topsheet 10C has a great number of perforations 4 through the valleys at a prescribed interval in the longitudinal direction. Each perforation is defined by the two nonwoven fabrics 11 and 12 sticking from the surface side 10a to the back side 10b of the topsheet 10C. The inner wall 41 of each perforation 4 is formed by a surface contiguous to the surface side 10a. That is, the perforation is three-dimensional. The three-dimensional shape of the perforation 4 may be cylindrical or conical with its diameter gradually increasing from the surface side 10a toward the back side 10b but is preferably inverted conical with its diameter gradually decreasing from the surface side 10a toward the back side 10b as shown in FIGS. 10 and 11. The shape of the perforation hole in a plan view is not particularly limited and may be, for example, elliptic, triangular, or rectangular but is preferably circular, an isotropic shape, as shown in FIG. 11 in view of improvement on softness of the topsheet 10C and shape stability of the bottom edge 42 of the perforation 4. Because the perforations 4 are formed by piercing pins through a non-perforated stack of nonwoven fabrics, the bottom edge 42 of the perforations 4, where the nonwoven fabrics have been strongly compressed, has a higher density than the ridges 2, particularly the top portion 26 of the ridges 2, that have undergone no or little compression. The term "density" as used here is the density of the topsheet 10C or the stack of the nonwoven fabrics making the topsheet 10C. With respect to the individual nonwoven fabrics, too, the density of each of the nonwoven fabrics 11 and 12 is higher at the bottom edge 42 than at the ridges 2, particularly the top portion 26 of the ridges 2. It is preferred for the lower nonwoven fabric 12 to have a higher density than the upper nonwoven fabric 11. The density of the topsheet 10C or the stack of the nonwoven fabrics making the topsheet 10C gradually decreases from the bottom edge 42 of the perforations 4 toward the top portion 26 of the ridges 2.

In the topsheet 10C of the fourth embodiment, the bottom edges 42 of the perforations 4 and the ridges 2 (particularly their top portions 26) correspond high density portions and low density portions having different densities, respectively. The topsheet 10C has a larger amount of a skin care agent 5 applied to the ridges 2 (particularly their top portions 26), which are low density portions, than to the bottom edges 42, which are high density portions. The skin care agent 5 is attached to, for example, the shaded regions in FIGS. 11 and 12.

The topsheet 10C of the fourth embodiment is assembled into a diaper with its upper nonwoven fabric 11 facing the wearer's skin and the lower nonwoven fabric 12 facing the absorbent member 40.

In the fourth embodiment, too, a larger amount of a skin care agent is present in the ridges 2 (particularly the top portions 26), which are low density portions, than in the bottom edges 42 of the perforations 4, which are high density portions. Since the ridges 2 (low density portions), particularly their top portions 26 have larger interfiber spaces than the bottom edges 42 of the perforations 4 (high density portions), the topsheet 10C is able to contain a larger amount of the skin care agent in the low density portions than in the high density portions. If the high density portions with smaller interfiber spaces are configured to contain a large amount of the skin care agent, it is likely that the skin care agent adversely affects the liquid permeability. Such a problem is less likely to occur when the skin care agent is held in the low density portions as in the present embodiment.

Since the topsheet 10C of the fourth embodiment contains a larger amount of a skin care agent in the low density portions than in the high density portions, both the low and the high density portion being distributed in the planar directions and/or the thickness direction (direction Z), the skin care agent is not only ready to transfer to the wearer's skin but also less likely to hinder a relatively highly viscous bodily discharge from wicking through the perforations into the absorbent member. Therefore, it is expected that the bodily discharges are quickly separated away from the skin and that the skin care agent is allowed to transfer sufficiently.

The sheet materials forming the two nonwoven fabrics 11 and 12 may be any of sheet materials conventionally used to make the topsheet of absorbent articles, such as disposable diapers and sanitary napkins. For example, various sheet materials described supra for use as the two nonwoven fabrics 11 and 12 of the topsheet 10 of the first embodiment may be used. Each of the two nonwoven fabrics 11 and 12 before being stacked and integrated into a unitary sheet may be a non-consolidated web.

The topsheets 10B and 10C of the third and the fourth embodiment may be produced by forming a three-dimensional sheet material (having no skin care agent) in a known method and applying a skin care agent 5 using, for example, a coating roller set on one side of the three-dimensional sheet material at such a position as to make contact only with the surface of the three-dimensional sheet.

The three-dimensional sheet material used to make the topsheet 10B of the third embodiment is exemplified by the three-dimensional sheet materials described in JP 2002-187228A and JP2004-345357A. The three-dimensional sheet material used to make the topsheet 10C of the fourth embodiment is exemplified by the one described in JP2004-275296A.

An example of the method for forming a three dimensional sheet material 10C' for use to make the topsheet 10C will be described with reference to FIG. 13.

Figure 13:
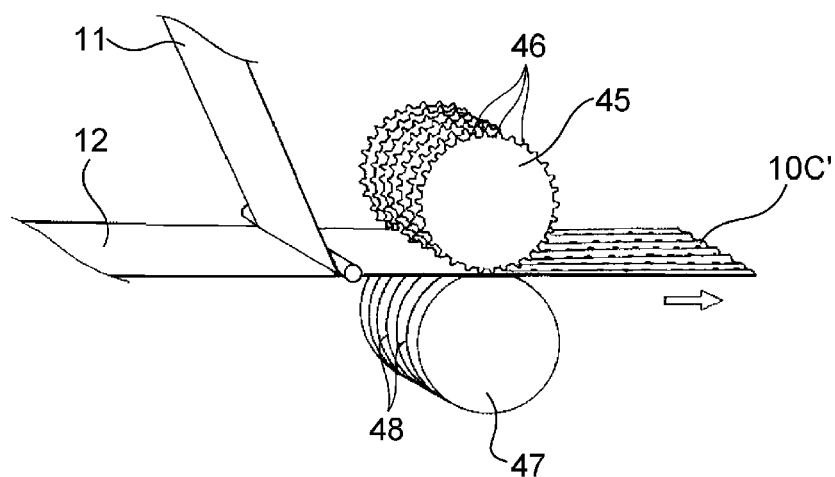
FIG. 13 schematically illustrates the step of forming a three-dimensional sheet material in a preferred method for making the topsheet used in the fourth embodiment.

In the method shown in FIG. 13, nonwoven fabric 11 and 12 fed from the respective unshown rolls are superposed on each other, and the stack of the nonwoven fabric 11, 12 is passed between the nip of a first embossing element 45 and a second embossing element 47 to create perforations 4 (perf-embossing). A three dimensional sheet material 10C' that is preferably used to produce the topsheet 10C is thus obtained.

The first embossing element 45 for creating perforations is a pin roller having many pyramidal or conical perforating pins arranged in lines along the machine direction and rows along the cross-machine direction. The second embossing element 47 is a corrugated roller having ridges 48 fitting in grooves between the lines of pins on the first embossing element 45. As a result of the ridges of the corrugated roller (the second embossing element 47) fitting in between the lines of the pins of the pin roller (the first embossing element 45), ridges 2 and valleys 3 continuous in the machine direction of the topsheet 10 are formed. At the same time, the pins of the pin roller penetrate the nonwoven fabrics 11 and 12 in the valleys 3 to form perforations 4. The nonwoven fabrics 11 and 12 are strongly pressed together at the bottom edge 42 of the individual perforations 4.

The pins are preferably heated to bond the fibers by fusion in the bottom edges 42. The perf-embossing operation using the first and the second embossing element and preferred conditions therefor may be the same as those described in JP6-330443A filed by the assignee of the instant application.

Application of a skin care agent to make the topsheets of the third and fourth embodiment may be performed by, for example, a method in which a first roller is partly dipped in a skin care agent in a container and rotates to transfer the skin care agent to a second roller set in contact with the peripheral surface of the first roller, and then the second roller rotates to transfer the skin care agent to the low density portions of a three dimensional sheet material which is in light contact with the second roller.

While the present invention has been described based on its preferred embodiments, it should be understood that the invention is not limited to these embodiments and various changes and modifications can be made therein without departing from the spirit and scope thereof.

For example, application of a skin care agent is accomplished by various techniques other than the methods described above, such as die coating, slot spraying, curtain spraying, melt blowing, spiral spraying, gravure coating, and bead coating.

The high density portions and the low density portions may be arranged in the planar directions in a pattern different from those of the first and second embodiment and may be arranged in the thickness direction in a pattern different from those of the third and fourth embodiment.

While the debossed portions in the second embodiment and the fusion bonds in the third embodiment are arranged in a dot pattern, they may be arranged otherwise, such as in a lattice pattern.

EXAMPLES

The invention will now be illustrated in greater detail with reference to Examples, but the invention is not deemed to be limited thereto.

Example 1

(1) Formation of Three Dimensional Sheet Material

A three dimensional sheet material 10' was formed using air-through nonwoven fabrics each having a basis weight of 18 g/m$^2$ as an upper and a lower nonwoven fabric 11 and 12 through the apparatus shown in FIG. 4. The upper nonwoven fabric 11 was a double-layered nonwoven fabric obtained by through-air bonding a stack of a first carded web of PE sheath/PET core conjugate fibers with a thickness of 2.2 dtex and a second carded web of PE sheath/PET core conjugate fibers with a thickness of 4.4 dtex.

The double-layered nonwoven fabric as the nonwoven fabric 11 was used with its second web side facing the nonwoven fabric 12. The lower nonwoven fabric 12 was an air-through nonwoven fabric made of PE sheath/PET core conjugate fibers with a thickness of 2.3 dtex.

Both the first and the second roller were heated to 135° C. The air-through nonwoven fabrics are fabrics obtained by treating a carded web with hot air in a through-air system to fusion-bond the fibers at their intersections.

The resulting three dimensional sheet material 10' had the following density profile.
Density of protruded regions 14A:
Density of upper nonwoven fabric (density of the top of the protrusions): 0.056 g/m$^3$ (thickness: 0.32 mm)
Density of lower nonwoven fabric: 0.064 g/m$^3$ (thickness: 0.28 mm)

Overall density of the protruded regions 14A: 0.030 g/m³ (basis weight: 36 g/m²; thickness: 1.2 mm)
Density of bonded regions 13A:
Overall density of bonded regions 13A: 0.26 g/m³ (basis weight: 36 g/m²; thickness: 0.14 mm)

The overall density of the protruded regions 14A and that of the bonded regions 13A were calculated by dividing the thickness of the three dimensional sheet material 10' in the protruded regions 14A (the height of the hollow space between the nonwoven fabrics 11 and 12 is excluded) and the thickness of the three dimensional sheet material 10' in the bonded regions 13A, respectively, by the basis weight of the three dimensional sheet material 10' (=36 g/m²).

The interfiber distance of the nonwoven fabric 11 at the top of the protrusions 14 was larger than that at the bonded portions 13.

(2) Application of Skin Care Agent

A skin care agent was sprayed onto the three dimensional sheet material 10' from the side of the upper nonwoven fabric 11 in the manner shown in FIG. 5 under the conditions below.
Composition of Skin Care Agent:
An equal mass mixture of a diamide derivative of formula (I) and stearyl alcohol (St-OH), in which the diamide derivative was represented by formula (II):

[Chem. 2]

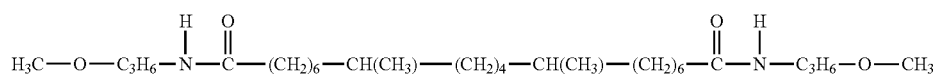

(II)

Figure 14:
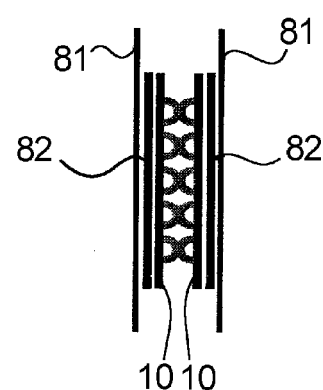
FIG. 14 is a schematic cross-sectional view of the topsheet of Example being stored in a loaded condition.

Basis weight of skin care agent applied: 0.5 g/m²
Distance between three dimensional sheet material 10' and spray gun: 50 mm
Gun air pressure: 0.3 MPa
Processing speed (running speed of three dimensional sheet material 10'): 50 m/min (3) Storage of Topsheet Sample Stored in Unloaded Condition:
The topsheet having the skin care agent applied thereto was sandwiched between sheets of release paper without winding into a roll and stored at 23° C. and 50% RH.
Sample Stored in Loaded Condition:
Assuming the condition in which the topsheet as assembled into a diaper is compression-packaged in a bag for sale, the topsheet 10 having the skin care agent applied thereto was sandwiched between sheets of release paper 81 as shown in FIG. 14 and stored under a load of about 5 kPa at 40° C. and 80% RH for 3 days. In FIG. 14, the numeral 82 indicates tissue paper having a basis weight of 16 g/m². The topsheet was removed, and the topsheet as sandwiched in between the sheets of released paper was then stored at 23° C. and 50% RH. The load of 5 kPa is a pressure generally assumed to be applied to individual diapers when a number of diapers are stacked and compression packaged in a bag for sale.

(4) Determination of Skin Care Agent

Each of the sample stored in unloaded condition and the sample stored in loaded condition was cut with scissors to make 1 to 2 mm side square specimens, specifically, a first specimen cut out of the upper nonwoven fabric 11 from a protruded region 14A; a second specimen cut out of the lower nonwoven fabric 12 from the protruded region 14A; and a third specimen cut out of a bonded region 13A where the upper nonwoven fabric 11 and the lower nonwoven fabric 12 were bonded together.

Figure 15:
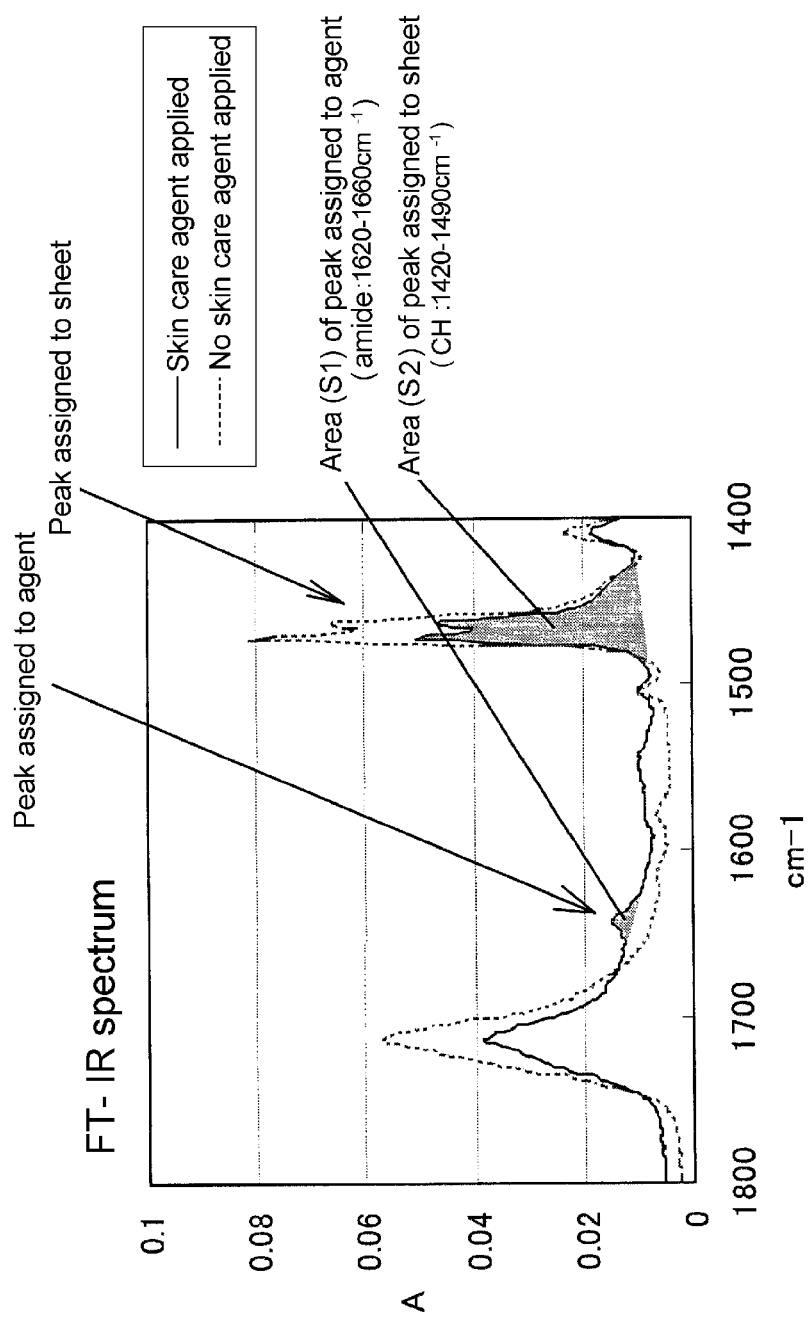
FIG. 15 is an FT-IR spectrum.

Each specimen was analyzed by the hereinafter described second method (FT-IR method) to obtain a ratio of area S1 of the absorption peak of the amide group assigned to the skin care agent (1600 to 1670 cm⁻¹) to area S2 of the C—H absorption peak assigned to the sheet (1400 to 1500 cm⁻¹), S1/S2 (see FIG. 15). The specimen was scanned by IR on its skin facing side (the upper side in FIG. 3). The results obtained are shown in FIG. 16.

Figure 16:
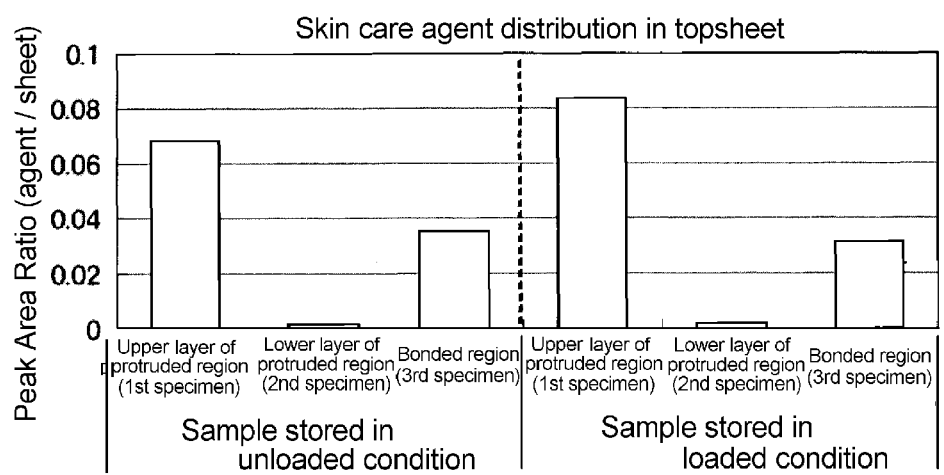
FIG. 16 is a graph showing the results of evaluation in Example.

The results shown in FIG. 16 demonstrate that the topsheet of Example 1 contains a larger amount of the skin care agent in its protruded region 14A, which is a low density portion, than in the bonded region 13A, which is a high density portion. A comparison within the protruded region 14A reveals the presence of a larger amount of the skin care agent in the upper nonwoven fabric 11 than in the lower nonwoven fabric 12.
Method for Measuring Density Profile of Topsheet:
The high density portion and the low density portion of a topsheet are identified by determining the interfiber distance in nonwoven fabric. It is possible to identify a portion having a small interfiber distance to be a high density portion and a portion having a relatively large interfiber distance compared with the high density portion to be a low density portion.

The density measurement starts with preparation of a cut surface passing through a target high or low density portion taking care not to destroy the sample structure by using a safety razor Product No. FAS-10 (from Feather Safety Razor Co., Ltd.) or a like tool. To avoid structure destruction due to pressure application, it is preferred that the sample be sufficiently frozen in liquid nitrogen before being cut. The cut surface is observed under a scanning electron microscope (SEM) to take a micrograph of the target portion at magnifications of 500 to 1000. The electron microscopy was performed using JCM-5100 from JEOL, Ltd. under conditions of platinum sputtering time of 30 seconds and an accelerating voltage of 10 kV. A region of the target portion in each enlarged SEM image in which three to seven fibers extend in the horizontal direction of the image (i.e., a planar direction of the sheet) is analyzed on an image analyzer NEWQUBE ver. 4.20 from NEXUS to obtain the distance between nearest centroids of the fibers. The measurement is made over substantially the entire thickness of the target portion, making sure that there are no overlaps of the distance between nearest centroids. The measurement is taken on at least 3, preferably 5, more preferably 10, cut surfaces of the topsheet to obtain an average. The distance between nearest centroids is used to calculate the interfiber distance.

As for the topsheets of which the high density portions are fowled by compression, such as embossing, like those of the first and the second embodiment, the high or low density portions are regarded as distinguishable by the electron microscopic observation described. Then, the density of the high or low density portion may be calculated from the thickness of the portion in the SEM image and the basis weight of the topsheet.

Method for Determining the Amount of Skin Care Agent in Topsheet:

The method for determining the amount of the skin care agent in each of the high and the low density portion of the topsheet will be described below.

First Method:

The amount of the skin care agent present in the high and the low density portion can be determined by IR spectroscopy. A comparison between a portion with a larger amount of a skin care agent and a portion with a smaller amount of a skin care agent can be made by comparing the IR absorption peak intensities in their IR spectra. That is, a portion showing a higher IR absorption peak intensity (a higher IR absorption) proves to have a larger amount of a skin care agent.

The skin care agent present in each portion may be quantitatively determined by obtaining a ratio of the IR absorption intensity assigned to the skin care agent of the high density portion to that of the low density portion and calculating the amount of the skin care agent in each portion from the ratio and the total amount of the skin care agent applied.

The IR spectroscopy is conveniently carried out by ATR spectroscopy. As long as the measuring range is sufficiently broad, a comparison can be made between the high density portion and the low density portion at any wavenumber of the absorption peaks (in the case of the diamide derivative, the peak at, for example, 3300 $cm^{-1}$ assigned to an amide group) of ATR IR spectra acquired by directly examining samples (ATR IR macroscopy; diameter: 2 to 3 mm). In the case of observing a very small portion, a microscope attachment (100 μm) may be used.

An example of determination is shown below.
IR absorption spectrophotometer: Spectrum One (with Multiscope), from Perkin Elmer
Macroscopy: A single-pass spectrum is acquired using a diamond ATR probe.
Microscopy: A germanium ATR probe is used.
Wavenumber resolution: 4 $cm^{-1}$
Number of times of integration: 4 (in macroscopy) or 16 (in microscopy)

Second Method:

The amount of the skin care agent present in the high and the low density portion can also be determined by FT-IR spectroscopy. A comparison between a portion with a larger amount of a skin care agent and a portion with a smaller amount of a skin care agent can be made by comparing ratios of the area of the absorption peak assigned to the skin care agent to the area of the absorption peak assigned to the topsheet in an FT-IR spectrum acquired. That is, a portion having a higher area ratio proves to contain a larger amount of the skin care agent.

The FT-IR spectroscopy is conveniently carried out by ATR spectroscopy. A comparison can be made between any absorption peaks acquired by direct IR spectroscopy. In the case of, for example, a PE/PET topsheet having a diamide derivative applied thereto, the peak at 1600 to 1670 $cm^{-1}$ assigned to an amide group and the peak at 1400 to 1500 $cm^{-1}$ assigned to the C—H absorption of the sheet may be compared.
IR absorption spectrophotometer: Spectrum One, from Perkin Elmer
Wavenumber resolution: 4 $cm^{-1}$
Number of times of integration: 16

The absorbent articles of the invention include not only disposable diapers but sanitary napkins, panty liners (vaginal discharge sheets), incontinence pads, hygiene pads, and nursing pads.

The invention claimed is:

1. An absorbent article comprising a liquid permeable topsheet, a liquid impermeable or water repellent backsheet, and an absorbent member arranged between the topsheet and the backsheet,
   the topsheet being formed of a nonwoven sheet having high density portions and low density portions, each high density portion being different in density from each low density portion,
   the high density portions and the low density portions being arranged in planar directions of the topsheet,
   the topsheet comprising protrusions bulging toward the skin of a wearer, each having a top portion, and depressions located between adjacent protrusions, each having a bottom, each low density portion corresponding to the top portion of a protrusion, and each high density portion being located in the bottom of a depression,
   the high density portions containing a skin care agent, and the low density portions having a larger amount of the skin care agent applied thereto than the high density portions,
   wherein the topsheet comprises an upper nonwoven fabric adapted to face the skin of a wearer and a lower nonwoven fabric on the side facing the absorbent member, and
   wherein an amount of skin care agent per same size area attached to the upper nonwoven fabric is larger than an amount of skin care agent per same size area attached to the lower nonwoven fabric.

2. The absorbent article according to claim 1, wherein the bottoms of the depressions have a bonded region having said upper nonwoven fabric and said lower nonwoven fabric bonded to one another, and the high density portions correspond to the bonded region.

3. The absorbent article according to claim 2, wherein an amount of skin care agent per same size area attached to the lower nonwoven fabric in each low density portion is larger than an amount of skin care agent per same size area attached to the lower nonwoven fabric in the high density portions.

4. The absorbent article according to claim 1, wherein each high density portion is located between low density portions adjacent each high density portion in both a planar direction of the topsheet and a direction perpendicular to said planar direction.

5. The absorbent article according to claim 1, wherein the low density portions have a larger area than the high density portions in a plan view of the topsheet.

6. The absorbent article according to claim 1, wherein the low density portions are spacedly arrayed in a first planar direction to make a plurality of lines of the low density portions and the lines are arrayed in a second planar direction perpendicular to the first planar direction such that there is no area without a low density portion over a total length in the second direction.

7. The absorbent article according to claim 1, wherein the upper nonwoven fabric adapted to face the skin of a wearer and the lower nonwoven fabric on the side facing the absorbent member have bonded portions in which the upper nonwoven fabric and the lower nonwoven fabric are bonded to each other, and the upper nonwoven fabric forming the protrusions bulging toward the skin of a wearer in a portion other than the bonded portions, with each protrusion being hollow.

8. The absorbent article according to claim 7, wherein an amount of skin care agent per same size area attached to the lower nonwoven fabric in each low density portion is larger than an amount of skin care agent per same size area attached to the lower nonwoven fabric in the high density portions.

9. The absorbent article according to claim 1, wherein each of the low density portions is surrounded by high density portions.

10. The absorbent article according to claim 1, wherein each protrusion has a height of 1 to 4 mm.

11. The absorbent article according to claim 1, wherein each protrusion has a plan-view shape of a circle, an elongated circle, a rhombus, or a triangle.

* * * * *